(12) United States Patent
Long et al.

(10) Patent No.: US 7,002,055 B2
(45) Date of Patent: Feb. 21, 2006

(54) TOILET TRAINING ARTICLE CONTAINING A FOAMING AGENT

(75) Inventors: Andrew Long, Appleton, WI (US); Shirlee Ann Weber, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/822,930

(22) Filed: Apr. 13, 2004

(65) Prior Publication Data

US 2005/0228349 A1   Oct. 13, 2005

(51) Int. Cl.
*A61F 13/15*   (2006.01)
(52) U.S. Cl. ............ 604/361; 604/385.12; 604/385.01
(58) Field of Classification Search ............... 604/361, 604/364, 369, 304, 308, 145; 206/219; 252/3; 602/46; 128/287
See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,512,528 A * | 5/1970 | Skora et al. ............... 604/369 |
| 3,542,615 A | 11/1970 | Doto et al. |
| 3,692,618 A | 9/1972 | Dorschner et al. |
| 3,802,817 A | 4/1974 | Matsuki et al. |
| 3,849,241 A | 11/1974 | Butin et al. |
| 3,881,491 A * | 5/1975 | Whyte ......................... 604/370 |
| 3,921,232 A * | 11/1975 | Whyte ......................... 428/12 |
| 4,289,794 A | 9/1981 | Kleiner et al. |
| 4,340,563 A | 7/1982 | Appel et al. |
| 4,704,116 A | 11/1987 | Enloe |
| 4,790,836 A | 12/1988 | Brecher |
| 4,940,464 A | 7/1990 | Van Gompel et al. |
| 5,277,180 A * | 1/1994 | Angelillo et al. ........... 607/114 |
| 5,342,535 A | 8/1994 | Ramirez et al. |
| 5,649,914 A * | 7/1997 | Glaug et al. ................. 604/361 |
| 5,658,268 A | 8/1997 | Johns et al. |
| 5,681,298 A | 10/1997 | Brunner et al. |
| 5,702,376 A | 12/1997 | Glaug et al. |
| 5,702,377 A | 12/1997 | Collier, IV et al. |
| 5,733,272 A | 3/1998 | Brunner et al. |
| 5,766,389 A | 6/1998 | Brandon et al. |
| 5,797,892 A | 8/1998 | Glaug et al. |
| 5,885,264 A | 3/1999 | Matsushita |
| 5,891,124 A | 4/1999 | Nomura et al. |

(Continued)

FOREIGN PATENT DOCUMENTS

JP   11-178854   7/1999

(Continued)

OTHER PUBLICATIONS

International Search Report for PCT/US01/29557.

(Continued)

*Primary Examiner*—Tatyana Zalukaeva
*Assistant Examiner*—L C Hill
(74) *Attorney, Agent, or Firm*—Senniger Powers

(57) ABSTRACT

Absorbent articles for alerting a wearer to urination are disclosed. The absorbent articles comprise a bodyside liner, an absorbent core, and a urine-permeable inflatable envelope located between the bodyside liner and the absorbent core. The envelope comprises a surfactant and a system capable of generating a gas upon being wetted with urine. Upon urination, a foam is formed in the envelope such that the envelope inflates and causes the bodyside liner to press up against the skin of the wearer to alert the wearer to urination.

53 Claims, 2 Drawing Sheets

U.S. PATENT DOCUMENTS

| | | | |
|---|---|---|---|
| 5,997,520 A * | 12/1999 | Ahr et al. | 604/385.12 |
| 6,369,290 B1 | 4/2002 | Glaug et al. | |
| 6,451,331 B1 | 9/2002 | Slavtcheff et al. | |
| 6,576,810 B1 | 6/2003 | Underhill et al. | |
| 6,657,100 B1 * | 12/2003 | Underhill et al. | 604/361 |
| 2003/0139713 A1 | 7/2003 | Olson et al. | |
| 2003/0153884 A1 | 8/2003 | Underhill, et al. | |
| 2004/0102335 A1 * | 5/2004 | Carrick et al. | 508/192 |
| 2004/0231977 A1 * | 11/2004 | Roselle et al. | 204/242 |

FOREIGN PATENT DOCUMENTS

| | | |
|---|---|---|
| WO | WO 94/24994 A1 | 11/1994 |
| WO | WO 00/37009 | 6/2000 |
| WO | WO 01/56542 A1 | 8/2001 |
| WO | WO 01/60299 A1 | 8/2001 |
| WO | WO 0156542 A1 * | 9/2001 |
| WO | WO 0351258 A1 * | 11/2002 |
| WO | WO 03/051258 A1 | 6/2003 |

OTHER PUBLICATIONS

Pugh, R., Handbook of Applied Surface and Colloid Chemistry, 2002, Chapter 2 (pp. 23-43), John Wiley & Sons,Ltd., West Sussex, England.

International Search Report from PCT/US2005/001262 dated Mar. 19, 2005.

* cited by examiner

TOILET TRAINING ARTICLE CONTAINING A FOAMING AGENT

BACKGROUND OF INVENTION

The present invention relates to an absorbent article for assisting children in toilet training. More specifically, the present invention is directed to an absorbent article comprising a bodyside liner, an absorbent core, and a urine-permeable inflatable envelope containing a gas producing system and a surfactant. Upon urination by a wearer, the inflatable envelope swells with foam and pushes the bodyside liner against the skin of the wearer to alert the wearer that urination has occurred.

Disposable absorbent articles, such as training pants, are useful in toilet training children. Typically, these types of undergarments are similar to washable, cloth underwear in how they are put on and worn, yet also provide an absorbent function like diapers to draw and retain urine away from the skin of the wearer. Training pants provide a child undergoing toilet training with an undergarment that eases the transition from diapers to washable, cloth underwear as they become more confident in their ability to use the toilet independently.

In order to use the toilet independently, a child must first recognize when urination has occurred so that this bodily function may be controlled. This recognition can represent a substantial hurdle in the training process as urination may often occur during an activity that distracts the child sufficiently so that the child does not notice urination. Also, a child's ability to recognize when urination occurs may be hampered by the improved performance of disposable absorbent undergarments that quickly draw and retain urine away from the wearer's skin after an insult occurs.

Many believe that a child must feel the sensation of wetness on the skin after urination in order to facilitate awareness of this bodily function and promote timely use of the toilet so as to avoid the uncomfortable feeling that otherwise follows. Although this belief is embraced by many, such practice may expose a child to an increased risk of skin irritations and rashes caused by prolonged and repeated contact with urine.

Several attempts have been made at providing toilet training aids that alert a child that urination has occurred. For example, pads adapted for releasable attachment to the crotch and/or buttocks region of a disposable toilet training pant, diaper, or other undergarment and including a temperature change member and/or a dimensional change member that provide a temperature change or dimensional change sensation when contacted with urine to alert the child wearing the undergarment that urination has occurred have been fabricated. Also, absorbent articles have been disclosed that when first insulted have a high initial surface moisture value or wet feel to alert the child that urination has occurred. This initial wetness lasts only a short time after which the surface moisture value drops to a lower level resulting in a more comfortable, drier feeling to the child. Additionally, absorbent articles having fading graphics upon urination have been disclosed to alert a wearer to urination.

Although there has been some progress in toilet training aids, there continues to be a need for simple, effective articles that alert children that urination has occurred. It would be desirable for such articles to provide effective, immediate feedback to the child that lasts over an extended period of time without subjecting the skin of the wearer to any detrimental effects.

SUMMARY OF THE INVENTION

The present invention is directed to absorbent articles that aid children in toilet training. Specifically, the present invention is directed to absorbent articles that comprise a bodyside liner, an absorbent core, and a urine-permeable inflatable envelope located between the bodyside liner and absorbent core. The inflatable envelope comprises a surfactant and a system capable of producing a gas upon being wetted with urine. Upon urination by a wearer, the system and surfactant are wetted and a gas is produced in the envelope. This gas, in combination with the surfactant, causes a foam comprised of bubbles to form in the inflatable envelope and causes the envelope to swell and push up the bodyside liner against the wearer's skin to alert the wearer that urination has occurred. The inflatable envelope may optionally include a temperature change agent that causes the produced foam to feel cool against the skin. In this case, the wearer is alerted to urination by both a pressure against the skin and a cooling sensation against the skin.

As such, the present invention is directed to an absorbent article for alerting a wearer to urination. The article comprises a bodyside liner, an absorbent core, and a urine-permeable inflatable envelope located between the bodyside liner and the absorbent core. The inflatable envelope comprises a surfactant and a system capable of generating carbon dioxide upon being wetted with urine.

The present invention is further directed to an absorbent article for alerting a wearer to urination. The article comprises a bodyside liner, an absorbent core, and a urine-permeable inflatable envelope located between the bodyside liner and the absorbent core. The urine-permeable inflatable envelope comprises a surfactant and a system capable of generating a gas upon being wetted with urine.

The present invention is further directed to an absorbent article for alerting a wearer to urination. The article comprises a bodyside liner, an absorbent core, and a urine-permeable inflatable envelope located between the bodyside liner and the absorbent core. The inflatable envelope comprises a surfactant, a system capable of generating carbon dioxide upon being wetted with urine, and a temperature change agent.

Other features of the present invention will be in part apparent and in part pointed out hereinafter.

DETAILED DESCRIPTION OF THE PREFERRED EMBODIMENT

The present invention is generally directed to absorbent products for assisting children in toilet training. The absorbent products, such as toilet training pants, generally comprise a bodyside liner, an absorbent core, and a urine-permeable inflatable envelope positioned between the bodyside liner and the absorbent core. The inflatable envelope comprises a surfactant and a system that, upon wetting with urine, produces a gas, such as carbon dioxide. The gas produced upon the wetting with urine interacts with the surfactant to produce a foam that inflates the envelope. The inflated envelope pushes against the bodyside liner and causes the bodyside liner to press against the skin of the wearer to alert the wearer that urination has occurred. Optionally, the inflatable envelope may comprise a temperature change agent that makes the bodyside liner feel cool against the skin of the wearer. Desirably, the foam may be produced over an extended period of time such that if the bubbles are burst when the wearer sits or otherwise exerts pressure on the envelope, they will reform upon the release of the pressure to again alert the wearer to the urination.

Figure 1:
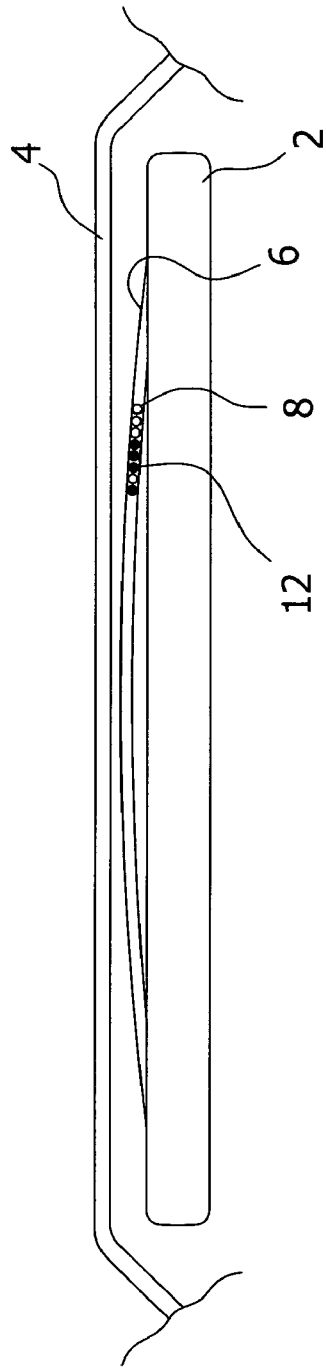
FIG. 1 is a cross section of an absorbent article comprising a non-inflated envelope.

With reference to FIG. 1, the absorbent articles described herein comprise a bodyside liner 4, an absorbent core 2, and a urine-permeable inflatable envelope 6 positioned between the bodyside liner 4 and the absorbent core 2. The urine-permeable inflatable envelope 6 comprises a gas producing system 8 and a surfactant 12. As used herein, the term "urine-permeable" refers to a porous material that is water-permeable due to the flow of water and other aqueous liquids, such as urine, through the pores.

The bodyside liner 4 is suitably compliant, soft feeling, and non-irritating to the wearer's skin. Further, the bodyside liner 4 can be less hydrophilic than the absorbent core 2 described below to present a relatively dry surface to the wearer and permit liquid to readily penetrate through its thickness. Alternatively, the bodyside liner 4 can be more hydrophilic or can have essentially the same affinity for moisture as the absorbent core 2 to present a relatively wet surface to the wearer to increase the sensation of being wet. This wet sensation can sometimes be useful as a training aid. The hydrophilic/hydrophobic properties can be varied across the length, width and/or depth of the bodyside liner 4 and absorbent core 2 to achieve the desired wetness sensation and/or leakage performance.

The bodyside liner 4 can be manufactured from a wide selection of web materials, such as synthetic fibers (e.g., polyester or polypropylene fibers), natural fibers (e.g., wood or cotton fibers), a combination of natural and synthetic fibers, porous foams, reticulated foams, apertured plastic films, and the like. Various woven and nonwoven fabrics can be used for the bodyside liner 4. For example, the bodyside liner 4 can be composed of a meltblown or spunbonded web of polyolefin fibers. The bodyside liner 4 can also be a bonded-carded web composed of natural and/or synthetic fibers. The bodyside liner 4 can be composed of a substantially hydrophobic material, and the hydrophobic material can, optionally be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C. and Glucopan 220UP from Henkel Corporation of Ambler, Pa., in an active ratio of 3:1. The surfactant can be applied by any conventional means, such as spraying, printing, brush coating, and the like. The surfactant can be applied to the entire bodyside liner 4 or can be selectively applied to particular sections of the bodyside liner 4, such as the medial section along the longitudinal center line.

A suitable liquid permeable bodyside liner 4 is a nonwoven bicomponent web having a basis weight of about 27 grams per square meter (gsm). The nonwoven bicomponent can be a spunbond bicomponent web, or a bonded carded bicomponent web. Suitable bicomponent fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, and the like.

The absorbent core 2 can be any structure that is generally compressible, conformable, non-irritating to the wearer's skin, and capable of absorbing and retaining liquid body exudates. The absorbent core 2 may be manufactured in a wide variety of sizes and shapes, and from a wide variety of absorbent materials commonly used in the art. For example, the absorbent core 2 may comprise a matrix of absorbent fibers, and more particularly hydrophilic fibers, such as a web of cellulosic fluff. In a particular embodiment, the absorbent core 2 comprises a matrix of cellulosic fluff, such as wood pulp fluff, and superabsorbent particles. The wood pulp fluff can be exchanged with synthetic, polymeric, meltblown fibers, or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent core 2 to better contain and absorb body exudates. The concentration of the superabsorbent particles can also vary through the thickness of the absorbent core 2. Alternatively, the absorbent core 2 can comprise a laminate of fibrous webs and superabsorbent material or other suitable means of maintaining the superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers (e.g., sodium neutralized polyacrylic acid). Suitable superabsorbent materials are available from various commercial vendors, such as Dow Chemical Company located in Midland, Mich., and Stockhausen GmbH & Co. located in the Federal Republic of Germany.

In one embodiment, the absorbent core 2 may comprise a blend of wood pulp fluff and superabsorbent material. One preferred type of pulp fluff is identified with the trade designation CR1654, commercially available from U.S. Alliance, Childersburg, Ala., and is a bleached, highly absorbent sulfate wood pulp containing primarily soft wood fibers and about 16 percent hardwood fibers. Typically, the superabsorbent material is present in the absorbent core 2 in an amount of from about 0 to about 90 weight percent based on a total weight of the absorbent core 2. The absorbent core 2 suitably has a density within the range of from about 0.10 to about 0.35 grams per cubic centimeter. The absorbent core 2 may or may not be wrapped or encompassed by a suitable wrapsheet that may help maintain the integrity and/or shape of the absorbent core 2.

The inflatable envelope 6 that is positioned between the bodyside liner 4 and the absorbent core 2 comprises an inflatable liquid permeable envelope. The envelope 6 may be suitably formed from either woven or nonwoven substrates that are substantially liquid permeable to allow liquids, such as urine, to pass therethrough and contact the gas producing system and surfactant described herein. In one embodiment, the inflatable liquid permeable envelope 6 may be formed from a 20 gsm spunbond nonwoven material available from Kimberly-Clark Corporation, Neenah, Wis. More particularly, a pair of opposed sheets of such material may be ultrasonically or otherwise bonded together along an edge margin about the periphery of the envelope 6 so as to seal the envelope. The envelope 6 may be either adhesively or thermally bonded to the absorbent core 2 and/or the bodyside liner 4 to stabilize the envelope during use. The envelope 6 is sized, configured, and positioned in the absorbent article in such a manner that the envelope 6 is free to swell without substantial interference from other components of the absorbent article.

It should be understood that the envelope 6 could be fabricated from materials other than a spunbond nonwoven so long as at least a portion of the envelope 6 is sufficiently liquid permeable to permit liquid body exudates to permeate therethrough into the interior of the envelope 6 for contact with the gas producing systems and surfactants described below.

Figure 2:
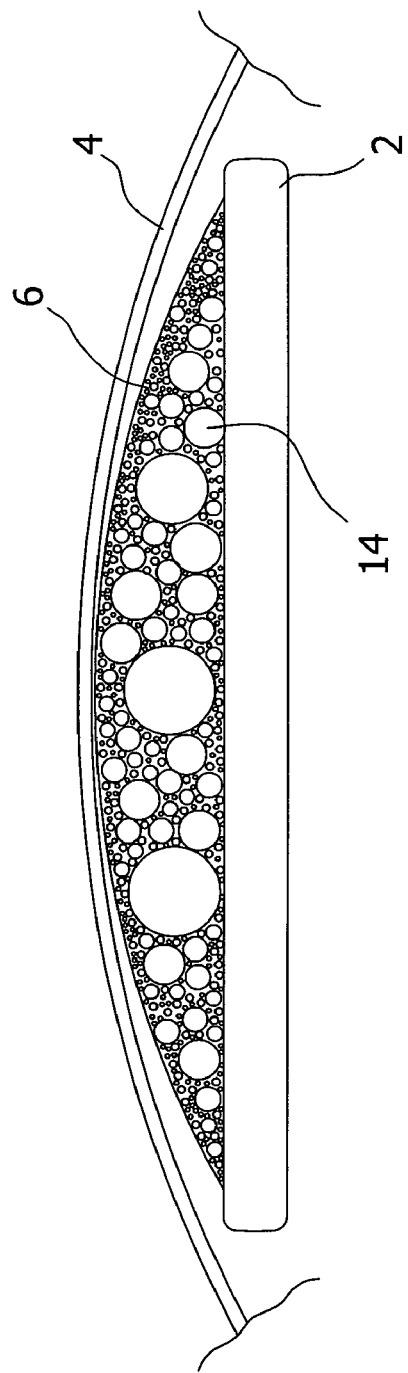
FIG. 2 is a cross section of an absorbent article comprising an inflated envelope.

As noted above, the urine-permeable inflatable envelope comprises a system capable of generating a gas upon being wetted with urine. The gas that is produced in the envelope upon the wetting interacts with one or more surfactants, which are discussed below, and produces foam that inflates the envelope and causes it to press the bodyside liner against the skin of the wearer to alert the wearer to urination. Referring now to FIG. 2, there is shown an absorbent core 2, bodyside liner 4, and urine permeable inflatable envelope 6, which is filled with foam 14. As shown in FIG. 2, the inflated envelope 6 pushes against the bodyside liner 4 and distorts the bodyside liner 4. The distortion causes the bodyside liner to press against the skin of the wearer to alert the wearer to urination.

In one embodiment, the system capable of generating gas upon being wetted with urine, which is located in the urine-permeable inflatable envelope, comprises at least one acid and at least one base. The acid and base react together upon being wetted with urine to produce a gas that may be, for example, carbon dioxide gas. The exact gas produced by the gas producing system is not critical, so long as the gas produced is substantially non-harmful to the skin of the wearer.

One example of a suitable acid/base combination is shown in equation (1):

$$NaHCO_3 + KHC_4H_4O_6 \rightarrow KNaC_4H_4O_6 + H_2O + CO_2 \quad (1)$$

In equation (1), sodium bicarbonate and potassium bitartrate react in the presence of a liquid (urine) to form carbon dioxide gas and by-products. The production of carbon dioxide, in combination with a surfactant, allows the formation of a foam in the urine-permeable inflatable envelope.

Another example of a suitable acid/base combination for use in the urine-permeable inflatable envelope is shown in equation (2):

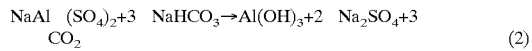

$$NaAl(SO_4)_2 + 3\ NaHCO_3 \rightarrow Al(OH)_3 + 2\ Na_2SO_4 + 3\ CO_2 \quad (2)$$

In equation (2), sodium aluminum sulfate and sodium bicarbonate react in the presence of liquid (urine) to form carbon dioxide gas and by-products. Other acids that can be used in combination with sodium bicarbonate to produce a gas in accordance with the present invention include ascorbic, lactic, glycolic, malic, tartaric, and fumaric.

In order to fully protect against any damage to the skin by the acid/base reaction, it is desirable that the resulting acid/base mixture in the presence of the urine should have a resulting pH of from about 4.5 to about 7.5. One skilled in the art will recognize that a buffering agent could be utilized in combination with the acid/base combination to help control the resulting pH of the acid/base mixture in the urine. One skilled in the art will also recognize that appropriate stoichiometric amounts of acids and bases would need to be utilized to obtain a mixture that when wetted with urine will produce a pH in the above range.

The urine-permeable inflatable envelope comprises a suitable amount of acid and base such that a suitable amount of gas is produced upon urination to produce the desired amount of bubbles and foam. Suitably, the envelope may comprise from about 0.1 grams to about 15 grams of acid and from about 0.1 grams to about 15 grams of base.

In another embodiment, the system capable of generating a gas upon being wetted with urine comprises a urine-soluble effervescent solid material produced in such a manner such that a pressurized gas is trapped within cells located in the solid material. When the solid material having pressurized gas-containing cells is contacted with urine, it begins to dissolve and the pressurized gas is released from the cells during dissolution of the solid material. This gas can interact with the surfactant also located in the urine-permeable inflatable envelope and produce a foam and bubbles that inflate the envelope as described herein.

In this embodiment, the urine-soluble effervescent solid material may comprise a sugar compound such as a mono-saccharide, di-saccharide, or poly-saccharide that has been infused with a gas that is substantially non-reactive with human skin. Suitable gases for infusion into a solid material include, for example, carbon dioxide, air, nitrogen, argon, helium, other substantially inert gases, and combinations thereof. Specific examples of saccharides that can be used in accordance with the present invention include glucose, fructose, sucrose, lactose, maltose, dextrin, cyclodextrin, and the like, alone or in combination. Also, a mixture of sucrose with corn syrup (containing glucose, maltose, and dextrin) can be used in accordance with this embodiment of the present invention to produce a gas-containing effervescent agent. Other examples of compounds that are capable of being prepared in such a manner as to trap pressurized gas in cells include, for example, water soluble compounds such as salts, alkali halides, and alkaline earth metal halides. Specific salts useful in the present invention include, for example, sodium chloride, potassium chloride, potassium bromide, lithium chloride, cesium chloride, and the like. Typically, the cells containing the pressurized gas have a diameter of from about 5 micrometers to about 100 micrometers.

The substantially non-reactive gas can be infused into the cells of the urine-soluble solid material to produce an effervescent agent useful in the present invention by first heating the starting material, such as a sugar, in a small amount of water until the material is dissolved. After dissolution of the material, the water is evaporated off leaving the material in a molten state. The molten material is then gasified by introducing a suitable gas, such as carbon dioxide, at a superatmospheric pressure into a sealed vessel containing the molten material. The molten material is agitated during gasification to ensure intimate contact between the molten material and the gas. Pressures of, for example, between about 50 psig (340 kPa) and about 1000 psig (6890 kPa) may be utilized to infuse the gas into the molten material. After gas infusion, the molten material is allowed to solidify while maintained in the sealed vessel to produce an effervescent agent. A suitable procedure of producing a gas containing solid material is fully set forth in U.S. Pat. No. 4,289,794, which is hereby incorporated by reference. The above procedure can produce solid effervescent agents containing cells of pressurized gas from about 50 psig (340 kPa) to about 900 psig (6200 kPa) which, when exposed to urine, allow the release of the trapped gas. This trapped gas, when released, can interact with the surfactant material in the envelope described herein. The envelope may suitably comprise from about 0.1 grams to about 15 grams of effervescent solid material containing a pressurized gas.

As noted above, the envelope additionally comprises a surfactant. The surfactant component located in the urine-permeable inflatable envelope is present as a foaming agent. When a gas, such as carbon dioxide, is produced upon urination from the gas generating system located in the envelope, the gas interacts with the surfactant and a foam comprised of bubbles is produced. These bubbles inflate the envelope and cause it to swell and push against the bodyside liner which, in turn, pushes against the skin of the wearer to alert the wearer to the urination.

The surfactant used is not critical so long as it does not substantially irritate the skin upon contact. A wide variety of surfactants may be suitable for use in accordance with the present invention. For example, suitable surfactants include anionic surfactants, nonionic surfactants, amphoteric surfactants, cationic surfactants, and combinations thereof. Examples of suitable anionic surfactants include alkyl benzene sulfonates, alkyl sulfates, alkyl ether sulfates, sulfosuccinates, and combinations thereof. Examples of suitable nonionic surfactants include ethoxylated alcohols, fatty acid alkanolamides, ethoxylated alkanolamides, amine oxides, and combinations thereof. Examples of suitable amphoteric surfactants include alkyl betaines, amidobetaines, and combinations thereof. Examples of suitable cationic surfactants include alkylammonium halides. Generally, the envelope will comprise from about 0.1 grams to about 15 grams of surfactant.

In one embodiment of the present invention, the components comprising the system capable of generating a gas, such as carbon dioxide, upon being wetted with urine and/or the surfactant present in the urine-permeable inflatable envelope may be encapsulated in a urine-soluble shell material prior to introduction into the envelope. For example, if the system capable of generating a gas upon being wetted with urine comprises an acid and a base, the acid and the base may be separately encapsulated in a urine-soluble encapsulation material to keep the components separated until urination. Alternatively, the acid and base components may be encapsulated together if reactivity between the acid and the base in the absence of a liquid is not a concern. The surfactant may be separately encapsulated, or may be encapsulated with the acid and/or the base. Additionally, encapsulation may be used with gas impregnated effervescent agents alone or in combination with the surfactant.

The shell material used for encapsulation may be suitably constructed of a material such that it will release the encapsulated material (i.e., the acid, base, effervescent agent and/or surfactant) upon contact with urine. The urine may cause the shell material to solubilize, disperse, swell, disintegrate, or may be urine permeable such that it disintegrates or discharges the encapsulated material upon contact with urine. Suitable shell materials include cellulose-based polymeric materials (e.g., ethyl cellulose), carbohydrate-based materials (e.g., starches and sugars) and materials derived therefrom (e.g., dextrins and cyclodextrins) as well as other materials compatible with human tissues.

The shell thickness may vary depending upon the material encapsulated, and is generally manufactured to allow the encapsulated component to be covered by a thin layer of encapsulation material, which may be a monolayer or thicker laminate, or may be a composite layer. The layer should be thick enough to resist cracking or breaking of the shell during handling or shipping of the product or during wear which would result in breakage of the encapsulating material. The material should also be constructed such that humidity from atmospheric conditions during storage, shipment, or wear will not cause a breakdown of the microencapsulation layer.

In addition to a system capable of generating a gas and a surfactant, the urine-permeable inflatable envelope may optionally comprise a temperature change agent. The temperature change agent facilitates a cold sensation against the wearer's skin upon urination. This cold sensation works in combination with the pressure exerted against the skin by the bodyside liner to alert the wearer to urination. When a temperature change agent is included, the gas, which forms the bubbles and creates the foam within the inflatable envelope, carries the cold from the temperature change agent to the surface of the skin. The temperature change is caused by an absorption of heat by the temperature change agent from the urine.

The temperature change agent suitably absorbs heat when contacted with an aqueous solution, such as urine. The mechanism by which this is accomplished may be the dissolution of the temperature change agent in the aqueous solution, the swelling of the agent in the aqueous solution, and/or the reaction of the agent in the aqueous solution. In particular embodiments, the temperature change agent is suitably in the form of particles that have a substantial energy difference between a dissolved state and a crystalline state, so that energy in the form of heat is absorbed from the environment upon contact with an aqueous solution, such as urine, and subsequent dissolution.

While a wide variety of temperature change agents may cause a temperature change of an aqueous solution when contacted therewith, the selection of a particular temperature change agent and the determination of the amount to be introduced into the inflatable envelope is based at least in part on the desired temperature change to be experienced by the wearer. For example, the temperature change agent suitably provides a temperature change between dry skin temperature prior to the urine insult and the skin temperature after the urine insult between about 5 and about 25 degrees Fahrenheit (about −15 to about −4 degrees Centigrade).

As noted above, the temperature change agents suitable for use in the inflatable envelope described herein include those that dissolve in an aqueous solution. The solubility of such temperature change agents is suitably in the range of from about 0.1 to about 3 grams of water per gram of agent, and more particularly from about 0.1 to about 2 grams of water per gram of agent.

Suitable temperature change agents include endothermic materials such as salt hydrates such as sodium acetate ($H_2O$), sodium carbonate ($10H_2O$), sodium sulfate ($10H_2O$), sodium thiosulfate ($5H_2O$), and sodium phosphate ($10H_2O$); anhydrous salts such as ammonium nitrate, potassium nitrate, ammonium chloride, potassium chloride, sodium bromide, magnesium chloride, calcium chloride, magnesium sulfate, and sodium nitrate; organic compounds such as urea, xylitol and other sugars, and the like. Generally, the inflatable envelope will comprise from about 0.1 grams to about 15 grams of temperature change agent.

As noted above, the absorbent core component of the absorbent articles described herein may comprise superabsorbent materials to assist in the absorption of the urine into the absorbent core and away from the skin of the wearer. In one embodiment of the present invention, it is desirable that all superabsorbent material located in the absorbent core component of the absorbent articles be located relatively deep in the absorbent core and away from the urine-permeable inflatable envelope. This may be desirable in some embodiments, such as an embodiment when a temperature change agent is utilized, as superabsorbent materials, upon swelling with urine, tend to hold or retain heat associated with the urine and create small "hot pockets" within the absorbent core. If the superabsorbent materials are located at or near the urine-permeable inflatable envelope-absorbent core intersection, the heat retained by the superabsorbent materials may be transferred into the envelope and minimize or eliminate any cooling sensation which may be transferred to the skin of the wearer through the use of a temperature change agent.

In order to substantially reduce or eliminate the potential for the swollen superabsorbent materials to transfer heat into the urine-permeable inflatable envelope, the superabsorbent materials may suitably be located in the absorbent core at least about ¼ inch (0.64 cm), and suitably at least about ⅛ inch (0.32 cm) from the urine-permeable inflatable envelope-absorbent core intersection. At this distance, the amount of heat held by the superabsorbent materials will not substantially be transferred into the urine-permeable inflatable envelope and will not substantially interfere with any cooling sensation.

Figure 3:
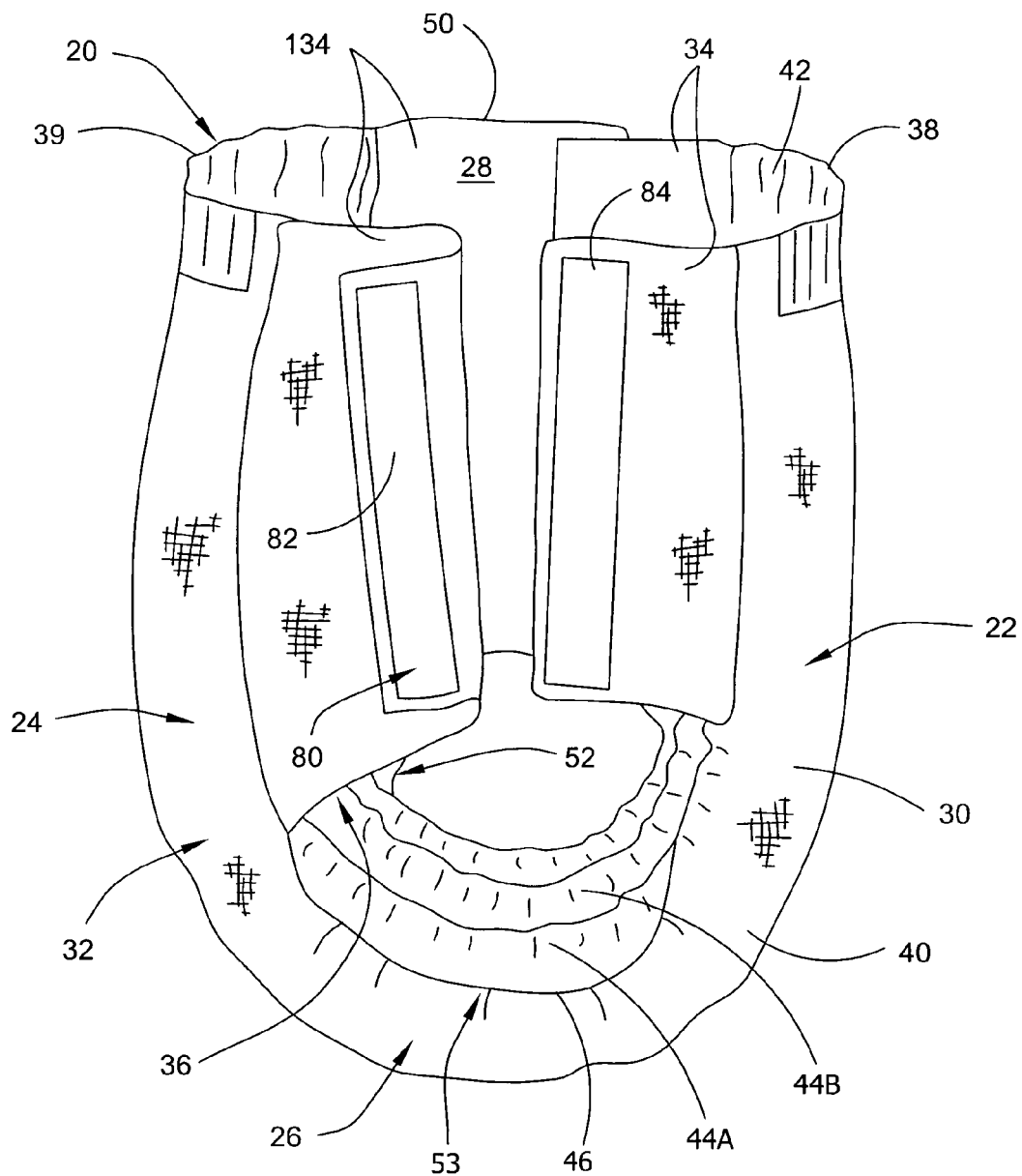
FIG. 3 is a side perspective of an absorbent article suitable for use in the present invention shown in the form of a pair of training pants.

Referring now to FIG. 3, one particular example of a suitable absorbent article of the present invention is illustrated herein in the form of children's toilet training pants and indicated in its entirety by the reference numeral 20. By way of illustration only, various materials and methods for constructing training pants such as the pants 20 of FIG. 3 are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., each of which is incorporated herein by reference.

The pair of training pants 20 is illustrated in FIG. 3 in a partially fastened condition and comprises longitudinal end regions, further referred to herein as a front waist region 22 and a back waist region 24, and a center region, further referred to herein as a crotch region 26, extending longitudinally between and interconnecting the front and back waist regions. The pants 20 also has an inner surface 28 which faces the wearer and an outer surface 30 which faces away from the wearer. The front and back waist regions 22, 24 comprise those portions of the pants 20 that, during wear, wholly or partially cover or encircle the waist or mid-lower torso of the wearer. The crotch region 26 generally comprises that portion of the pants 20 which, during wear, is positioned between the legs of the wearer and covers the lower torso and crotch of the wearer. The crotch region 26 is a suitable region for placement of the inflatable envelope as described herein.

The illustrated pants 20 comprises a central absorbent assembly, generally indicated at 32, a pair of laterally opposite front side panels 34 extending outward therefrom at the front waist region 22 and a pair of laterally opposite back side panels 134 extending outward therefrom at the back waist region 24. The central absorbent assembly 32 of the illustrated embodiment is generally rectangular. However, it is contemplated that the central absorbent assembly 32 may be other than rectangular, such as hourglass shaped, T-shaped, I-shaped, and the like without departing from the scope of this invention.

The central absorbent assembly 32 comprises an outer cover 40 (broadly referred to herein as a substrate) and a bodyside liner 42 (also broadly referred to herein as a substrate) arranged in generally superposed relationship with the outer cover. The liner 42 is suitably adapted (i.e., positioned relative to the other components of the pants 20) for contiguous relationship with the wearer's skin when the pants are worn. The absorbent assembly 32 further comprises a pair of absorbent structures 44a, 44b disposed between the outer cover 40 and the bodyside liner 42 for absorbing liquid body exudates released by the wearer. As noted above, the inflatable envelope (not shown in FIG. 3) may be suitably positioned between the absorbent assembly 32 and the bodyside liner 42 as described herein. A pair of containment flaps 46 is secured to the bodyside liner 42 in laterally spaced relationship with each other to inhibit the transverse flow of body exudates on the liner to the side edges 36 of the absorbent assembly 32. Longitudinally opposite ends of the central absorbent assembly 32 of the illustrated embodiment respectively form portions of the front and back waist edges 38 and 39 of the pants 20, and laterally opposite side edges of the absorbent assembly form portions of the side edges 36 of the training pants.

The outer cover 40 is substantially liquid impermeable to inhibit body exudates against leaking from the pants 20 and wetting articles, such as bed sheets and clothing, as well as the wearer and caregiver. As an example, the outer cover 40 may comprise a single layer, multiple layers, laminates, spunbond fabrics, films, meltblown fabrics, elastic netting, microporous web, bonded carded webs or foams comprised at least in part of elastomeric or polymeric materials.

The bodyside liner 42 presents a body-facing surface which isolates the wearer's skin from liquids retained by the absorbent structures 44a, 44b and is suitably compliant, soft-feeling, and non-irritating to the wearer's skin. Further, the bodyside liner 42 can be less hydrophilic than the absorbent structures 44a, 44b and is sufficiently porous to be liquid permeable, permitting liquid to readily penetrate through its thickness to reach the absorbent structures. A suitable bodyside liner 42 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers.

The bodyside liner 42 and outer cover 40 are suitably attached to one another, for example, by being directly attached to each other such as by affixing the outer cover 40 directly to the liner 42, or by being indirectly attached to each other such as by affixing the bodyside liner to intermediate components of the pants 20 which in turn are affixed to the outer cover.

The containment flaps 46 each have at least one flap elastic member 53 secured thereto along an unattached edge of the flap so that the flaps assume a generally upright configuration in at least the crotch region 26 of the training pants 20 to form a seal against the wearer's body. The containment flaps 46 are suitably located adjacent the side edges 36 of the pants 20, and can extend longitudinally along the entire length of the absorbent assembly 32 or may extend only partially along the length of the absorbent assembly. Suitable constructions and arrangements for the containment flaps 46 are generally well known to those skilled in the art and are described in U.S. Pat. No. 4,704,116 issued Nov. 3, 1987 to Enloe, which is incorporated herein by reference.

With the training pants 20 fastened as is partially illustrated in FIG. 3, the front and back side panels 34, 134 are fastened together by a fastening system 80 in a three-dimensional configuration of the pants to define a waist opening 50 and a pair of leg openings 52 of the pants. The fastening system 80 comprises laterally opposite first fastening components 82 adapted for refastenable engagement to corresponding second fastening components 84. The engaging elements of the first fastening components 82 are adapted to repeatedly engage and disengage corresponding engaging elements of the second fastening components 84 to releasably secure the pants 20 in its three-dimensional configuration. The fastening components 82, 84 can comprise any refastenable fasteners suitable for absorbent articles, such as adhesive fasteners, cohesive fasteners, mechanical fasteners, or the like.

The absorbent structures 44a, 44b (broadly referred to herein as inner and outer absorbent structures, respectively, based on the relative positions of the absorbent structures to the wearer of the pants 20) are suitably arranged in generally superposed relationship with each other between the outer cover 40 and the liner 42, and are more suitably arranged in generally overlapping relationship with each other. Each of the absorbent structures 44a, 44b is suitably compressible, conformable and capable of absorbing and retaining liquid body exudates released by the wearer. The absorbent structures 44a, 44b may be constructed of any of a number of well known materials suitable for taking in and retaining liquid body exudates.

In view of the above, it will be seen that the several objects of the invention are achieved and other advantageous results obtained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. An absorbent article for alerting a wearer to urination comprising a bodyside liner, an absorbent core, and a urine-permeable inflatable envelope located between the bodyside liner and the absorbent core, the urine-permeable inflatable envelope comprising a surfactant and a system capable of generating carbon dioxide upon being wetted with urine.

2. The absorbent article as set forth in claim 1 wherein the system capable of generating carbon dioxide upon being wetted with urine comprises an acid and a base.

3. The absorbent article as set forth in claim 2 wherein the acid is potassium bitartrate and the base is sodium bicarbonate.

4. The absorbent article as set forth in claim 2 wherein the acid is sodium aluminum sulfate and the base is sodium bicarbonate.

5. The absorbent article as set forth in claim 2 wherein the acid, base, and surfactant are encapsulated.

6. The absorbent article as set forth in claim 1 wherein the surfactant is selected from the group consisting of anionic surfactants, nonionic surfactants, amphoteric surfactants, cationic surfactants, and combinations thereof.

7. The absorbent article as set forth in claim 6 wherein the anionic surfactants are selected from the group consisting of alkyl benzene sulfonates, alkyl sulfates, alkyl ether sulfates, sulfosuccinates, and combinations thereof.

8. The absorbent article as set forth in claim 6 wherein the nonionic surfactants are selected from the group consisting of ethoxylated alcohols, fatty acid alkanolamides, ethoxylated alkanolamides, amine oxides, and combinations thereof.

9. The absorbent article as set forth in claim 6 wherein the amphoteric surfactants are selected from the group consisting of alkyl betaines, amidobetaines, and combinations thereof.

10. The absorbent article as set forth in claim 6 wherein the cationic surfactants are alkylammonium halides.

11. The absorbent article as set forth in claim 1 wherein the inflatable envelope comprises a spunbond nonwoven material.

12. The absorbent article as set forth in claim 1 wherein the inflatable envelope is attached to the absorbent core.

13. The absorbent article as set forth in claim 2 wherein the absorbent core comprises superabsorbent particles.

14. The absorbent article as set forth in claim 13 wherein the superabsorbent particles in the absorbent core are located at least about ⅛ inch from the inflatable envelope.

15. The absorbent article as set forth in claim 13 wherein the superabsorbent particles in the absorbent core are located at least about ¼ inch from the inflatable envelope.

16. The absorbent article as set forth in claim 2 wherein the urine-permeable inflatable envelope comprises from about 0.1 grams to about 15 grams of acid, from about 0.1 grams to about 15 grams of base, and from about 0.1 grams to about 15 grams of surfactant.

17. An absorbent article for alerting a wearer to urination comprising a bodyside liner, an absorbent core, and a urine-permeable inflatable envelope located between the bodyside liner and the absorbent core, the urine-permeable inflatable envelope comprising a surfactant and a system capable of generating a gas upon being wetted with urine.

18. The absorbent article as set forth in claim 17 wherein the system capable of generating a gas upon being wetted with urine comprises an effervescent solid material containing pressurized gas within cells located in the effervescent solid material.

19. The absorbent article as set forth in claim 18 wherein the effervescent solid material comprises a composition selected from the group consisting of sugars, salts, alkali halides, alkaline earth metal halides, and combinations thereof.

20. The absorbent article as set forth in claim 17 wherein the pressurized gas within the cells is selected from the group consisting of carbon dioxide, air, nitrogen, argon, helium, and combinations thereof.

21. The absorbent article as set forth in claim 18 wherein the effervescent solid material and surfactant are encapsulated.

22. The absorbent article as set forth in claim 17 wherein the surfactant is selected from the group consisting of anionic surfactants, nonionic surfactants, amphoteric surfactants, cationic surfactants, and combinations thereof.

23. The absorbent article as set forth in claim 22 wherein the anionic surfactants are selected from the group consisting of alkyl benzene sulfonates, alkyl sulfates, alkyl ether sulfates, sulfosuccinates, and combinations thereof.

24. The absorbent article as set forth in claim 22 wherein the nonionic surfactants are selected from the group consisting of ethoxylated alcohols, fatty acid alkanolamides, ethoxylated alkanolamides, amine oxides, and combinations thereof.

25. The absorbent article as set forth in claim 22 wherein the amphoteric surfactants are selected from the group consisting of alkyl betaines, amidobetaines, and combinations thereof.

26. The absorbent article as set forth in claim 22 wherein the cationic surfactants are alkylammonium halides.

27. The absorbent article as set forth in claim 17 wherein the inflatable envelope comprises a spunbond nonwoven material.

28. The absorbent article as set forth in claim 17 wherein the inflatable envelope is attached to the absorbent core.

29. The absorbent article as set forth in claim 18 wherein the absorbent core comprises superabsorbent particles.

30. The absorbent article as set forth in claim 29 wherein the superabsorbent particles in the absorbent core are located at least about 1/8 inch from the inflatable envelope.

31. The absorbent article as set forth in claim 29 wherein the superabsorbent particles in the absorbent core are located at least about 1/4 inch from the inflatable envelope.

32. The absorbent article as set forth in claim 18 wherein the urine-permeable inflatable envelope comprises from about 0.1 grams to about 15 grams of effervescent solid material and from about 0.1 grams to about 15 grams of surfactant.

33. An absorbent article for alerting a wearer to urination comprising a bodyside liner, an absorbent core, and a urine-permeable inflatable envelope located between the bodyside liner and the absorbent core, the inflatable envelope comprising a surfactant, a system capable of generating carbon dioxide upon being wetted with urine, and a temperature change agent.

34. The absorbent article as set forth in claim 33 wherein the system capable of generating carbon dioxide upon being wetted with urine comprises an acid and a base.

35. The absorbent article as set forth in claim 34 wherein the acid is potassium bitartrate and the base is sodium bicarbonate.

36. The absorbent article as set forth in claim 34 wherein the acid is sodium aluminum sulfate and the base is sodium bicarbonate.

37. The absorbent article as set forth in claim 34 wherein the acid, base, and surfactant are encapsulated.

38. The absorbent article as set forth in claim 33 wherein the surfactant is selected from the group consisting of anionic surfactants, nonionic surfactants, amphoteric surfactants, cationic surfactants, and combinations thereof.

39. The absorbent article as set forth in claim 38 wherein the anionic surfactants are selected from the group consisting of alkyl benzene sulfonates, alkyl sulfates, alkyl ether sulfates, sulfosuccinates, and combinations thereof.

40. The absorbent article as set forth in claim 38 wherein the nonionic surfactants are selected from the group consisting of ethoxylated alcohols, fatty acid alkanolamides, ethoxylated alkanolamides, amine oxides, and combinations thereof.

41. The absorbent article as set forth in claim 38 wherein the amphoteric surfactants are selected from the group consisting of alkyl betaines, amidobetaines, and combinations thereof.

42. The absorbent article as set forth in claim 38 wherein the cationic surfactants are alkylammonium halides.

43. The absorbent article as set forth in claim 33 wherein the inflatable envelope comprises a spunbond nonwoven material.

44. The absorbent article as set forth in claim 33 wherein the inflatable envelope is attached to the absorbent core.

45. The absorbent article as set forth in claim 34 wherein the absorbent core comprises superabsorbent particles.

46. The absorbent article as set forth in claim 45 wherein the superabsorbent particles in the absorbent core are located at least about 1/8 inch from the inflatable envelope.

47. The absorbent article as set forth in claim 45 wherein the superabsorbent particles in the absorbent core are located at least about 1/4 inch from the inflatable envelope.

48. The absorbent article as set forth in claim 34 wherein the urine-permeable inflatable envelope comprises from about 0.1 grams to about 15 grams of acid, from about 0.1 grams to about 15 grams of base, and from about 0.1 grams to about 15 grams of surfactant.

49. The absorbent article as set forth in claim 34 wherein the temperature change agent is selected from the group consisting of salt hydrates, anhydrous salts, and organic compounds.

50. The absorbent article as set forth in claim 49 wherein the salt hydrates are selected from the group consisting of sodium acetate ($H_2O$), sodium carbonate (10 $H_2O$), sodium sulfate (10 $H_2O$), sodium thiosulfate (5 $H_2O$) sodium phosphate (10 $H_2O$), and combinations thereof.

51. The absorbent article as set forth in claim 49 wherein the anhydrous salts are selected from the group consisting of ammonium nitrate, potassium nitrate, ammonium chloride, potassium chloride, sodium bromide, magnesium chloride, calcium chloride, magnesium sulfate, sodium nitrate, and combinations thereof.

52. The absorbent article as set forth in claim 49 wherein the organic compounds are selected from the group consisting of urea, a sugar, and combinations thereof.

53. The absorbent article as set forth in claim 52 wherein the sugar is xylitol.

* * * * *